US011890278B2

(12) United States Patent
Papke et al.

(10) Patent No.: US 11,890,278 B2
(45) Date of Patent: Feb. 6, 2024

(54) BETEL QUID CESSATION THERAPY WITH NICOTINE AND PILOCARPINE

(71) Applicant: University of Florida Research Foundation, Incorporated, Gainesville, FL (US)

(72) Inventors: Roger L. Papke, Gainesville, FL (US); Samuel Leslie Glatman, Yangon (MM)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/962,827

(22) PCT Filed: Jan. 17, 2019

(86) PCT No.: PCT/US2019/014074
§ 371 (c)(1),
(2) Date: Jul. 16, 2020

(87) PCT Pub. No.: WO2019/143857
PCT Pub. Date: Jul. 25, 2019

(65) Prior Publication Data
US 2021/0361640 A1    Nov. 25, 2021

Related U.S. Application Data

(60) Provisional application No. 62/618,359, filed on Jan. 17, 2018.

(51) Int. Cl.
*A61K 31/465*  (2006.01)
*A61K 31/4178* (2006.01)
*A61K 9/00*    (2006.01)
*A61P 25/30*   (2006.01)

(52) U.S. Cl.
CPC .......... *A61K 31/465* (2013.01); *A61K 9/0056* (2013.01); *A61K 31/4178* (2013.01); *A61P 25/30* (2018.01)

(58) Field of Classification Search
CPC .. A61K 31/4178; A61K 9/0058; A61K 36/75; A61K 9/0056; A61K 31/465; A61K 2300/00; A61P 25/30
See application file for complete search history.

(56) References Cited

U.S. PATENT DOCUMENTS

| | | | |
|---|---|---|---|
| 5,059,531 A | | 10/1991 | Reuther |
| 5,571,528 A | * | 11/1996 | Lee ...................... A61K 9/0058 |
| | | | 424/440 |
| 5,760,049 A | * | 6/1998 | Viner ..................... A61K 31/44 |
| | | | 514/291 |
| 6,166,032 A | * | 12/2000 | Viner ..................... A61K 31/46 |
| | | | 514/304 |
| 2005/0020641 A1 | | 1/2005 | Sellers et al. |
| 2006/0029665 A1 | * | 2/2006 | Singh ........................ A61P 1/00 |
| | | | 424/464 |
| 2009/0081291 A1 | | 3/2009 | Gin et al. |
| 2009/0081294 A1 | * | 3/2009 | Gin ........................... A61P 1/00 |
| | | | 424/747 |
| 2011/0195987 A1 | | 8/2011 | Najarian et al. |
| 2017/0135988 A1 | | 5/2017 | Goren et al. |

FOREIGN PATENT DOCUMENTS

WO    WO 2007/044937 A2    4/2007

OTHER PUBLICATIONS

International Search Report and Written Opinion dated Apr. 3, 2019 for Application No. PCT/US2017/014074.

* cited by examiner

*Primary Examiner* — Jianfeng Song
(74) *Attorney, Agent, or Firm* — Wolf, Greenfield & Sacks, P.C.

(57) ABSTRACT

Provided herein are compositions comprising nicotine, or a salt thereof, and pilocarpine, or a salt thereof, useful for reducing the use of betel quid and/or achieving betel quid cessation (e.g., replacement therapy). Also provided herein are methods of using the compositions in reducing the risk of developing or reducing the progression of a disease (e.g., cancer, oral disease, neurological disease, or painful condition). Compositions of the present invention may be administered to a subject with an addiction, e.g., a betel quid addiction, areca nut addiction, and/or nicotine addiction.

15 Claims, No Drawings

BETEL QUID CESSATION THERAPY WITH NICOTINE AND PILOCARPINE

CROSS REFERENCE TO RELATED APPLICATIONS

This application is a National Phase Application under 35 U.S.C. 371 of PCT International Application No. PCT/US2019/014074, filed Jan. 17, 2019, which claims priority to U.S. Provisional Application No. 62/618,359, filed Jan. 17, 2018, which applications are incorporated herein by reference in their entirety.

BACKGROUND OF THE INVENTION

Betel quids are used by as many as 600 million people in Asia; worldwide they are the fourth most widely used addictive substance, after alcohol, caffeine, and nicotine (Little & Papke, 2015). The primary psychoactive agent in betel quid preparations is believed to be arecoline, which comes from the fruit of the *Areca catechu* palm (Lord, Lim, Warnakulasuriya & Peters, 2002). In the betel quid, *Areca* nut fragments are wrapped in a leaf of the *Piper betle* vine with slaked lime, other flavorants, and often tobacco.

It is well known that there are two aspects to drug-taking behavior: short-term reward or euphoria, and ultimately the neurological change that leads to dependence (Koob & Le Moal, 2005). Betel quid users receive the short-term euphoric/stimulant effects as a result of the muscarinic cholinergic activity of alkaloids in the areca nut, mainly arecoline. In addition to muscarinic acetylcholine receptors (mAChRs), arecoline also stimulates, yet to a lesser degree, nicotinic acetylcholine receptors (nAChRs) that are associated with addiction.

Betel quid users are classifiable as drug dependent (Herzog, Murphy, Little, Suguitan, Pokhrel & Kawamoto, 2014; Lee et al., 2014; Winstock, Trivedy, Warnakulasuriya & Peters, 2000) and pay a cost in their personal health with high risk for cancers (Akhtar, 2013; Franke, Lai, Kawamoto, Pokhrel & Herzog, 2014; Kao & Lim, 2015; Song, Wan & Xu, 2015) and other oral disease (Lee et al., 2012). However, with no alternative to using betel quid which can provide a similar sensation (i.e., euphoria or stimulation), many people continue to use betel quid, despite the health concerns. Clearly, affordable therapies need to be developed that will manage betel quid withdrawal, craving, and relapse to betel quid use, without producing side-effects that limit compliance.

SUMMARY OF THE INVENTION

The invention described herein is based in part on the realization that compositions comprising pilocarpine could satisfy betel quid users. Pilocarpine, like arecoline, is a muscarinic acetylcholine receptor-specific agonist, and does not affect nicotinic acetylcholine receptors. Thus, in one aspect, the invention provides compositions comprising nicotine and pilocarpine. These compositions comprise a safer alternative to arecoline, which is suspected to be at least one of the carcinogenic components of the areca nut, leading to a higher risk of developing oral cancer and/or other oral diseases. See, e.g., Sharan R N et al. (2012) Association of Betel Nut with Carcinogenesis: Revisit with a Clinical Perspective. *PLoS ONE*, 7; e42759.

In one aspect, the present disclosure provides a composition comprising nicotine, or a salt thereof, and pilocarpine, or a salt thereof. In some embodiments, the composition consists essentially of nicotine, or a salt thereof, and pilocarpine, or a salt thereof. In some embodiments, the composition consists of nicotine, or a salt thereof, and pilocarpine, or a salt thereof. In some embodiments, the composition comprises an acceptable carrier, adjuvant, excipient, or buffer. In some embodiments, the composition is a pharmaceutical composition, optionally comprising a pharmaceutically acceptable carrier, adjuvant, excipient, or buffer.

In some embodiments, the composition comprises an additional therapeutic agent. In some embodiments, the additional therapeutic agent is an anti-addiction agent, an anti-smoking agent, or an anti-nicotine addiction agent. In some embodiments, the composition further comprises a gum base.

In some embodiments, the composition is formulated for oral administration. In some embodiments, the composition is a gum, oral spray, nasal spray, lozenge, or pouch product. In some embodiments, the composition is a gum.

In another aspect, provided herein is a composition comprising nicotine, or a salt thereof, pilocarpine, or a salt thereof, and optionally an acceptable carrier, adjuvant, excipient, or buffer for oral administration.

In yet another aspect, the present disclosure provides a method of making a composition comprising nicotine, or a salt thereof, pilocarpine, or a salt thereof, and optionally an acceptable carrier, adjuvant, buffer, or excipient, the method comprising adding pilocarpine, or a salt thereof, to an oral formulation comprising nicotine, or a salt thereof, thereby producing a composition comprising nicotine and pilocarpine.

In another aspect, the present disclosure provides a method of making a composition comprising nicotine, or a salt thereof, pilocarpine, or a salt thereof, and optionally a pharmaceutically acceptable carrier, adjuvant, buffer, or excipient, the method comprising adding pilocarpine, or a salt thereof, to an oral formulation comprising nicotine, or a salt thereof, thereby producing a composition comprising nicotine and pilocarpine.

In yet another aspect, provided herein is a method for reducing the risk of developing a disease, the method comprising administering to a subject an effective amount of a composition or pharmaceutical composition described herein. In some embodiments, the disease is associated with stimulation of nicotinic acetylcholinergic receptors (nAChRs), stimulation of muscarinic acetylcholinergic receptors (mAChRs), or stimulation of both nAChRs and mAChRs. In some embodiments, the disease is cancer, a neurological disease, an oral disease, or a painful condition. In some embodiments, the painful condition is pain associated with withdrawal symptoms from a drug addiction. In some embodiments, the neurological disease is an addiction.

In another aspect, provided herein is a method for reducing the risk of developing a disease, the method comprising administering to a subject an effective amount of a composition or pharmaceutical composition produced by a method described herein. In some embodiments, the disease is associated with stimulation of nicotinic acetylcholinergic receptors (nAChRs), stimulation of muscarinic acetylcholinergic receptors (mAChRs), or stimulation of both nAChRs and mAChRs. In some embodiments, the disease is cancer, a neurological disease, an oral disease, or a painful condition. In some embodiments, the painful condition is pain associated with withdrawal symptoms from a drug addiction. In some embodiments, the neurological disease is an addiction.

In yet another aspect, the present disclosure provides a method for reducing betel quid and/or areca nut use, or the use of an equivalent preparation, the method comprising administering to a subject in need thereof an effective amount of a composition or pharmaceutical composition described herein.

In another aspect, the present disclosure provides a method for reducing betel quid and/or areca nut use, or the use of an equivalent preparation, the method comprising administering to a subject in need thereof an effective amount of a composition or pharmaceutical composition produced by a method described herein.

In yet another aspect, the present disclosure provides a method for achieving cessation of betel quid and/or areca nut use, or use of an equivalent preparation, the method comprising administering to a subject in need thereof an effective amount of a composition or pharmaceutical composition described herein.

In yet another aspect, the present disclosure provides a method for achieving cessation of betel quid and/or areca nut use, or use of an equivalent preparation, the method comprising administering to a subject in need thereof an effective amount of a composition or pharmaceutical composition produced by a method described herein.

In yet another aspect, provided herein is a method for eliminating and/or reducing the severity of withdrawal symptoms due to the cessation of betel quid and/or areca nut use, the method comprising administering to a subject in need thereof an effective amount of a composition or pharmaceutical composition described herein.

In yet another aspect, provided herein is a method for eliminating and/or reducing the severity of withdrawal symptoms due to the cessation of betel quid and/or areca nut use, the method comprising administering to a subject in need thereof an effective amount of a composition or pharmaceutical composition produced by a method described herein.

Also provided herein are kits comprising a composition provided herein, and optionally instructions for using the kit. In some embodiments, the kit comprises a composition comprising nicotine, or a salt thereof, and pilocarpine, or a salt thereof. In some embodiments, the kit comprises a single dose of the composition. In some embodiments, the kit comprises multiple doses of the composition.

All patents, patent applications, books, articles, documents, databases, websites, publications, references, etc., mentioned herein are incorporated by reference in their entirety. In case of a conflict between the specification and any of the incorporated references, the specification (including any amendments thereof), shall control. Applicants reserve the right to amend the specification based, e.g., on any of the incorporated material and/or to correct obvious errors. None of the content of the incorporated material shall limit the invention. Standard art-accepted meanings of terms are used herein unless indicated otherwise. Standard abbreviations for various terms are used herein.

The details of certain embodiments of the invention are set forth in the Detailed Description of Certain Embodiments of the Invention, as described below. Other features, objects, and advantages of the invention will be apparent from the Definitions, Examples, and Claims.

DEFINITIONS

Descriptions and certain information relating to various terms used in the present disclosure are collected herein for convenience.

The term "addiction" or "addiction disorder" includes any disorders involving addiction or addictive behavior in a subject. Examples of such disorders include, but are not limited to, smoking addiction; tobacco addiction; addiction to areca nut or areca nut products, areca nut leaves, roots, or seeds, areca nut extracts, or areca nut constituents; addiction to betel or betel products, betel leaves, roots, stems, or seeds, betel extracts, or betel constituents; or addiction to betel quid, paan, pan masala, gutka, or an equivalent.

The term "administer," "administering," or "administration" includes routes of introducing a composition provided herein to a subject to perform the composition's intended function. Administration may refer to implanting, absorbing, ingesting, injecting, inhaling, or otherwise introducing a composition described herein, or a pharmaceutical composition or formulation thereof, in or on a subject. A composition may be administered to the cell (e.g., "contacting") in vitro or in vivo. A composition may be administered to the subject in vivo via the appropriate route of administration. Examples of routes of administration that may be used include, but are not limited to, injection (e.g., subcutaneous, intravenous, parenterally, intraperitoneally, intrathecal), oral, inhalation, topical, rectal, and transdermal. The compositions or pharmaceutical preparations thereof (i.e., pharmaceutical compositions) may be administered in a form suitable for each administration route. For example, compositions may be administered in tablet, capsule, lozenge, or gum form; by inhalation through the nose or mouth; topically as an ointment, lotion, or in a patch; by suppository; or by injection or infusion. In some embodiments, a composition is administered orally. In some embodiments, a composition is administered in a tablet, lozenge, or gum. In some embodiments, the composition is administered via inhalation through the nose or through the mouth.

The term "agent" is used herein to refer to any substance, compound (e.g., molecule), supramolecular complex, material, or combination or mixture thereof. A compound may be any agent that can be represented by a chemical formula, chemical structure, or sequence. Example of agents, include, e.g., small molecules. In general, agents may be obtained using any suitable method known in the art. The ordinary skilled artisan will select an appropriate method based, e.g., on the nature of the agent. An agent may be at least partly purified. In some embodiments, an agent may be provided as part of a composition, which may contain, e.g., a counter-ion, aqueous or non-aqueous diluent or carrier, buffer, preservative, or other ingredient, in addition to the agent, in various embodiments. In some embodiments, an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)-isomers and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates [e.g., with water (i.e. hydrates) or common solvents] and/or may have different crystalline forms (e.g., polymorphs) or different tautomeric forms. Embodiments exhibiting such alternative protonation states, configurations, solvates, and forms are encompassed by the present disclosure where applicable. The term "agent" also encompasses a "therapeutic agent"

that provides some therapeutic benefit to a subject in need thereof. In some embodiments, the agent is a small molecule. In some embodiments, the agent is nicotine. In some embodiments, the agent is a nicotine salt. In some embodiments, the nicotine salt is nicotine bitartrate. In some embodiments, the agent is pilocarpine. In some embodiments, the agent is a pilocarpine salt. In some embodiments, the agent is pilocarpine hydrochloride.

The term "areca nut" refers to the fruit of the areca palm (*Areca catechu*). Areca nuts contain arecoline, a nicotinic acid-based alkaloid, which contributes to histologic changes in oral mucosa when administered to a subject. The areca nut described herein, e.g., in betel quid, can be in any form or obtained from any source. For example, the areca nut can be ripe or unripe, whole or sliced, raw, roasted, sun-dried, boiled, soaked in water, or fermented.

The term "betel" refers to a leaf of a vine belonging to the Piperaceae family (e.g., *Piper betle*). The betel described herein, e.g., in betel quid or paan, can be in any form or obtained from any source. For example, the betel leaf is often used to wrap areca nut and/or other ingredients in betel quid. Betel components, such as the stem or inflorescence (i.e., flower or pod), can be included in the betel quid.

The term "betel quid" refers to a chewing substance or a substance placed in the mouth that comprises betel (e.g., betel leaf) and areca nut and/or tobacco. The tobacco used in betel quid is often sun-dried, fermented, boiled with molasses, perfumed, or added as a concentrated extract (i.e., kiwam). In general, betel quid also contains slacked lime, which can be obtained from coral, shellfish, or quarried lime stone, for example. "Betel quid" encompasses various combinations of the ingredients, in various embodiments, for example, areca nut alone without any slacked lime or tobacco, chewing tobacco without any areca nut, areca nut with components of betel vine and other ingredients without tobacco, areca nut with components of betel vine and tobacco, etc. Other substances, such as *catechu* (e.g., from heartwood, leaves, or bark), spices (e.g., cloves, cardamom, aniseed), sweeteners (e.g., coconut, dried dates), and/or essences (e.g., rose essence, menthol, mint, rose petals), may also be added to the betel quid. In some embodiments, the betel quid does not comprise tobacco. In some embodiments, the betel quid does not comprise areca nut. In some embodiments, the "betel quid" is an "equivalent preparation", such as a "pan," "paan," "gutka," or any other preparation that comprises a betel constituent (e.g., betel leaves, roots, stems, inflorescence, or seeds; or betel extracts) and/or areca constituent (e.g., areca leaves, roots, or seeds; areca extracts; or areca nut). Often times, the chewing substance differs based upon individual preferences. For example, "pan masala" is a mixture of betel leaf, slacked lime, areca nut, clove, cardamom, mint, tobacco, essence, and other ingredients. "Gutka" is a preparation of crushed areca nut, tobacco, *catechu*, paraffin wax, slacked lime, and sweeteners or spices. In some embodiments, the betel quid, or equivalent product, does not comprise areca nut. In some embodiments, the betel quid, or equivalent product, does not comprise tobacco.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer is oral cancer. In some embodiments, the cancer is throat cancer. In some embodiments, the cancer is esophageal cancer. In some embodiments, the cancer is head and neck cancer. In some embodiments, the cancer is lung cancer.

The terms "cease," "ceasing," and "cessation" are used herein to refer to a process or action being brought to an end (i.e., stopping). For example, without wishing to be bound by any particular theory, cessation of betel quid use refers to a scenario in which a subject that uses betel quid routinely no longer uses betel quid upon administration of a composition described herein. In some embodiments, cessation refers to nearly complete reduction (e.g., reduced by about 100%) in a process or action (e.g., betel quid use).

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. The "effective amount" may be the "therapeutically effective amount" (i.e., the amount that provides the desired therapeutic effect). As will be appreciated by those of ordinary skill in this art, the absolute amount of a particular agent or composition that is effective may vary depending on such factors as the desired biological or pharmacological endpoint, the agent to be delivered, the target tissue, stage of the disease, etc. It will also be appreciated that the effective dosage of a composition may increase or decrease over the course of a particular treatment. Those of ordinary skill in the art will further understand that an "effective amount" may be administered to a subject in a single dose, or through use of multiple doses, in various embodiments. Dosage regimens may be adjusted to provide the optimum therapeutic response. An effective amount is also one in which any toxic or detrimental effects (e.g., side effects) of a composition are outweighed by the therapeutically beneficial effects. The "effective amount" may be the "prophylactically effective amount". The "prophylactically effective amount" refers to an amount of a composition described herein which is effective, upon single or multiple dose administration to the patient, in preventing or treating a disease or disorder. In some embodiments, the effective amount is the amount required to reduce a subject's desire to use (e.g., chew) betel quid. In some embodiments, the effective amount is the amount that achieves cessation of betel quid use. In some embodiments, the effective amount is the amount that reduces pain associated with a painful condition (e.g., pain associated with withdrawal symptoms of an addiction). In some embodiments, the effective amount is an amount that treats a neurological disease (e.g., addiction).

The term "muscarinic acetylcholine receptor" or "muscarinic acetylcholinergic receptor," abbreviated mAChRs, refers to acetylcholine receptor proteins that form G protein-receptor complexes in the cell membrane of neurons. These receptors are the main end-receptor stimulated by acetylcholine released from postganglionic fibers in the parasympathetic nervous system. Muscarinic acetylcholine receptors bind the natural product muscarine, and also respond to drugs and other small molecules, such as arecoline, pilocarpine, scopolamine. Ligands targeting mAChRs may be useful for the treatment of various diseases, including, but not limited to, Parkinson's disease, chronic obstructive pulmonary disease (COPD), and for the treatment of motion sickness.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP);

chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome. In some embodiments, the neurological disease (e.g., a disease of the central nervous system) is associated with the stimulation of nicotinic acetylcholinergic receptors (nAChRs), muscarinic acetylcholinergic receptors (mAChRs), or the stimulation of both nAChRs and mAChRs. In some embodiments, the neurological disease is Alzheimer's disease, Parkinson's disease, schizophrenia, Tourette's syndrome, anxiety, depression, or epilepsy.

The term "nicotinic acetylcholine receptor" or "nicotinic acetylcholinergic receptor," abbreviated nAChRs, refers to receptor protein ion channels that respond to the neurotransmitter acetylcholine. Nicotinic acetylcholine receptors also respond to drugs, such as the agonist nicotine. These receptors are found in the central and peripheral nervous system, muscle, and other tissues of many organisms, including humans. Activation of nAChRs results in the release of high local concentrations of neurotransmitters, effecting neighboring receptors, and also the release of neurotransmitters that effect distant receptors. As such, nAChRs contribute to the psychoactive properties of nicotine and other drugs of abuse and to the neuropathology of various diseases, including Alzheimer's, Parkinson's, and schizophrenia. See, e.g., Albuquerque E X et al. (2009) Mammalian Nicotinic Acetylcholine Receptors: From Structure to Function, *Physiol Rev.* 89; pp. 73-120, which is incorporated by reference herein.

"Nicotine" refers to naturally-occurring or synthetic nicotine. In some embodiments, the nicotine is naturally-occurring and derived from an extract obtained from a *Nicotiana* species (e.g., tobacco). In some embodiments, the nicotine is provided in an essentially pure form. In some embodiments, the nicotine is provided as an at least partially purified form (e.g., not contained within a plant structure, such as a tobacco leaf). In some embodiments, the nicotine is essentially free of other components obtained from tobacco. In some embodiments, the nicotine is a nicotine salt, solvate, hydrate, or prodrug. Exemplary nicotine salts include, but are not limited to, nicotine salts of tartrate (e.g., nicotine tartrate and nicotine bitartrate), chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; or nicotine salt hydrates (e.g., nicotine zinc chloride monohydrate), and the like. Additional organic acids that can form salts with nicotine include formic, acetic, propionic, isobutyric, butyric, alpha-methylbutyric, isovaleric, beta-methylvaleric, caproic, 2-furoic, phenylacetic, heptanoic, octanoic, nonanoic, oxalic, malonic, and glycolic acid, as well as other fatty acids having carbon chains of up to about 20 carbon atoms. In some embodiments, the nicotine, or salt thereof, is provided in a gum composition.

The term "oral disease" refers to diseases of the mouth (e.g., oral cavity, stoma), jaws (e.g., maxillae or gnath), and related structures (e.g., salivary glands, temporomandibular joints, facial muscles, and perioral skin), and symptoms associated therewith (e.g., irritation of the mucous membranes in the mouth). Exemplary oral diseases include, for example, periodontal disease, oral lesions (e.g., mouth ulcers, leukoplakia, erythroplakia), tooth loss, smokeless tobacco keratosis, gingival recession (i.e., receding gums), coronal decay, and root caries. A "periodontal disease", also known as periodontitis, gum disease, or pyorrhea, affects the tissues surrounding the teeth (e.g., gums). In some cases, periodontal disease involves the loss of the alveolar bone around the teeth and/or the loss of teeth. "Smokeless tobacco keratosis", also termed snuff dippers' keratosis, smokeless tobacco-associated keratosis, snuff pouch, snuff dipper's lesion, tobacco pouch keratosis, or spit tobacco keratosis, is a condition which develops on the oral mucosa (i.e., the lining of the mouth) in response to smokeless tobacco use and can increase the risk of oral cancer.

A "painful condition" includes, but is not limited to, neuropathic pain (e.g., peripheral neuropathic pain), central pain, deafferentiation pain, chronic pain (e.g., chronic nociceptive pain, and other forms of chronic pain such as stimulus of nociceptive receptors (nociceptive pain), acute pain (e.g., phantom and transient acute pain), noninflammatory pain, inflammatory pain, pain associated with cancer, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain, and the like. One or more of the painful conditions contemplated herein can comprise mixtures of various types of pain provided above and herein (e.g. nociceptive pain in combination with pain associated with withdrawal symptoms from drug addiction, etc.). In some embodiments, a particular pain can dominate (e.g., pain associated with withdrawal symptoms from drug addiction). In other embodiments, the painful condition comprises two or more types of pains without one dominating. A skilled clinician can determine the dosage to achieve a therapeutically effective amount for a particular subject based on the painful condition.

"Pilocarpine" refers to the small molecule extracted from the plant genus *Pilocarpus*. The most widely used pilocarpine in medicinal applications is derived from the leaves of *Pilocarpus microphyllus*. As used herein, "pilocarpine" may refer to free pilocarpine (e.g., free base form) or pilocarpine salts, solvates, hydrates, or prodrugs. Pilocarpine has generally been used as an ophthalmologic solution for the treatment of glaucoma, to reduce intraocular pressure spikes, or to reduce the possibility of glare at night after a patient has undergone implantation of phakic intraocular lenses. Pilocarpine is also used to stimulate sweat glands, as pilocarpine stimulates secretion of saliva and sweat. Thus, pilocarpine is also used to treat dry mouth (i.e., xerostomia).

The terms "reduce," "reduction," and "reducing" are used herein to describe a lower amount, extent, or number of occurrences. For example, without wishing to be bound by any particular theory, a reduction in a behavior (e.g., the desire to use betel quid) or in the number of occurrences (e.g., number of times a subject uses betel quid over a period of time) may be achieved upon administration of a composition described herein. In some embodiments, a subject's desire to use betel quid is reduced immediately after administration of an effective amount of a composition described herein. In some embodiments, a subject's desire to use betel quid is reduced for an extended period of time, for example, for 1 hour, 2 hours, 3 hours, 4 hours, 5 hours, 6 hours, 7 hours, 8 hours, 9 hours, 10 hours, 11 hours, 12 hours, 16 hours, 20 hours, 24 hours, 2 days, 3 days, 4 days, 5 days, 6 days, 7 days, or more, upon administration of an effective amount of composition described herein. In some embodiments, reduction in betel quid use is achieved after one dose. In some embodiments, reduction in betel quid use is achieved upon administration of multiple doses (e.g., 2 doses, 3 doses, 4 doses, 5 doses, 6 doses, 7 doses, 8 doses, 9 doses, 10 doses, 11 doses, 12 doses, or more). In some embodiments, reduction in betel quid use is achieved after one dose or after multiple doses over a time period of about 24 hours (i.e., one day).

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}\,alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g. a human, non-human primate, or rodent (e.g., mouse, rat, rabbit). In some embodiments, a subject is a human. In some embodiments, a subject has a disease or disorder relating to the stimulation of the nicotinic acetylcholinergic receptor (nAChR). In some embodiments, the subject has an addiction. In some embodiments, the subject uses betel quid and/or has an addiction to betel quid.

"Tobacco" as used herein refers to any product prepared from curing the leaves of a tobacco plant (e.g., a plant of the Nicotiana genus (e.g., Nicotiana tabacum, Nicotiana rustica) or Salanacaea family). "Tobacco" may refer to any preparation of tobacco, such as smoking preparations (e.g., cigarettes, cigars, pipe tobacco, shisha tobacco, and the like) or smokeless preparations (e.g., smokeless tobacco, snuff, snus, chewing tobacco, and dipping tobacco). Tobacco contains the alkaloid nicotine.

"Treat," "treating," "treatment," and similar terms as used herein in the context of treating a subject refer to providing medical management of a subject. Treatment may include, but is not limited to, administering an agent or composition comprising one or more agents (e.g., a pharmaceutical composition) to a subject. Treatment is typically undertaken in an effort to alter the course of a disease (which term is used to indicate any disease, disorder, syndrome or undesirable condition warranting or potentially warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease). In some embodiments, the disease is associated with stimulation of nicotinic acetylcholinergic receptors (nAChRs) and/or muscarinic acetylcholinergic receptors (mAChRs). In some embodiments, the disease is an addiction. In some embodiments, the addiction is a betel quid addiction, or an addiction to an ingredient in betel quid (e.g., areca nut, betel leaf, nicotine, etc.). In some embodiments, the disease is an oral disease. In some embodiments, the disease is cancer.

DETAILED DESCRIPTION OF CERTAIN EMBODIMENTS OF THE INVENTION

Compositions Comprising Nicotine and Pilocarpine

The invention described herein is based in part on the realization that compositions comprising pilocarpine could satisfy betel quid users. Pilocarpine, like arecoline, is a muscarinic acetylcholine receptor-specific agonist, and does not affect nicotinic acetylcholine receptors. Thus, in one aspect, the invention provides compositions comprising nicotine and pilocarpine. These compositions comprise a safer alternative to arecoline, which is suspected to be at least one of the carcinogenic components of the areca nut, leading to a higher risk of developing oral cancer and/or other oral diseases. See, e.g., Sharan R N et al. (2012) Association of Betel Nut with Carcinogenesis: Revisit with a Clinical Perspective. *PLoS ONE*, 7; e42759. Thus, compositions comprising nicotine and pilocarpine serve as a safer alternative (e.g., replacement therapy) for subjects who routinely use or are addicted to betel quid. In addition, the compositions described herein may prevent subjects from using betel quid or areca nut, thus serving as a preventative measure against the development of oral diseases or cancers (e.g., oral cancers, head and neck cancers, etc.).

In some aspects, provided herein is a composition comprising nicotine, or a salt thereof, and pilocarpine, or a salt thereof. In certain embodiments, the composition consists essentially of nicotine, or a salt thereof, and pilocarpine, or a salt thereof. In certain embodiments, the composition consists of nicotine, or a salt thereof, and pilocarpine, or a salt thereof. In some embodiments, the composition further comprises a pharmaceutically acceptable carrier, adjuvant, excipient, or buffer. In some embodiments, the composition comprises nicotine, or a salt thereof, pilocarpine, or a salt thereof, and a pharmaceutically acceptable carrier, adjuvant, excipient, or buffer. In some embodiments, the composition consists essentially of nicotine, or a salt thereof, pilocarpine, or a salt thereof, and a pharmaceutically acceptable carrier, adjuvant, excipient, or buffer. In some embodiments, the composition consists of nicotine, or a salt thereof, pilocarpine, or a salt thereof, and a pharmaceutically acceptable carrier, adjuvant, excipient, or buffer.

In some embodiments, the composition further comprises a gum base. The term "gum base" includes at least one gum base material which may be selected from the many water- and saliva-insoluble gum base materials known in the art. Illustrative examples of suitable polymers for gum bases include both natural and synthetic elastomers and rubbers, as well as mixtures thereof. Naturally-derived polymers include, for example, substances of plant origin such as chicle, jelutong, gutta percha and crown gum. Synthetic elastomers include, for example, butadiene-styrene copolymers, isobutylene and isoprene copolymers (e.g., "butyl rubber"), polyethylene, polyisobutylene, polyvinylesters (e.g., polyvinylacetate), and mixtures thereof. In general, the gum base should be selected to provide a final chewing gum composition which has a "soft" chew both at the onset of chewing, as well as towards to the end of the chewing process (e.g., about 20 minutes to about an hour). In addition, a gum base which facilitates sustained release of the active agent(s) (e.g., pilocarpine, nicotine) over the course of the chewing process may also be advantageous. In some embodiments, the gum base is a low to medium molecular weight polymer. In some embodiments, the gum base is a polymer with a molecular weight (MW) between 10,000 and 50,000. In some embodiments, the gum base comprises from about 40% to about 95% by weight of the total chewing gum composition. The gum base matrix may additionally comprise other ingredients known in the art, such as plasticizers and softeners, to help reduce the viscosity of the gum base to a desirable consistency and to improve the overall texture and bite. Non-limiting examples of these additional ingredients are lecithin, mono- and diglycerides, lanolin, stearic acid, sodium stearate, potassium stearate, glycerol triacetate, glycerol monostearate, and glycerin. Plasticizers and softeners are desirable as part of the formulation because, in addition to softening the primary gum base polymeric compound, they may also facilitate the release of the active agent(s) (e.g., pilocarpine, nicotine) upon chewing. In some embodiments, the plasticizers and/or softeners comprise from about 0.1% to about 20% by weight of the gum base formulation. In some embodiments, the plasticizers and/or softeners comprise from about 5% to about 15% by weight of the gum base formulation. In some embodiments, the gum base comprises waxes, such as beeswax or microcrystalline wax, and/or fats/oils, such as soybean or cottonseed oils. In some embodiments, the waxes and/or fats/oils comprise from about 0% to about 25% by weight of the gum base formulation. Other materials which may be included as part of the gum base matrix include elastomer solvents and filler material. These are typically selected from the group consisting of rosin and resin material typically utilized in the confectionery chewing gum industry. Non-limiting examples of rosin and resin material include methyl, glycerol, and pentaerythritol esters of rosins or modified rosins, such as hydrogenated, dimerized or polymerized rosins or mixtures thereof. Non-limiting examples of filler material are calcium carbonate, magnesium silicate (i.e., talc), dicalcium phosphate, alumina, aluminum hydroxide, and aluminum silicate.

In some embodiments, the pilocarpine is extracted from *Pilocarpus microphyllus*. In some embodiments, the pilocarpine is substantially pure. The term "substantially pure" refers to the purity of the compound (e.g., pilocarpine) which is at least about 95%, at least about 96%, at least about 97%, at least about 98%, at least about 98.5%, at least about 99%, at least about 99.5%, at least about 99.6%, at least about 99.7%, at least about 99.8%, at least about 99.9%, or at least about 100% pure as measured by an analytical technique (e.g., liquid chromatography, mass spectrometry, NMR spectrometry, etc.). In some embodiments, the pilocarpine is provided as a pilocarpine solution. In some embodiments, the pilocarpine solution is a pilocarpine hydrochloride solution. In some embodiments, the pilocarpine hydrochloride solution comprises between 1-5% pilocarpine hydrochloride. In some embodiments, the pilocarpine hydrochloride solution is a 1% pilocarpine hydrochloride solution. In some embodiments, the pilocarpine hydrochloride solution is a 2% pilocarpine hydrochloride solution. In some embodiments, the pilocarpine hydrochloride solution is a 4% pilocarpine hydrochloride solution. In some embodiments, the pilocarpine is provided as a solid. In some embodiments, the pilocarpine is provided as a powder comprising pilocarpine. In some embodiments, the powder comprises substantially pure pilocarpine, or a salt thereof. In some embodiments, the pilocarpine is provided as a tablet comprising pilocarpine. In some embodiments, the tablet comprises between 1-10 mg pilocarpine.

In some embodiments, the total pilocarpine concentration (i.e., the concentration of free pilocarpine, or the concentration of pilocarpine obtained from a salt thereof) in the composition is between 0.01% and 4%. In some embodiments, the total pilocarpine concentration in the composition is between 3% and 4%. In some embodiments, the total pilocarpine concentration in the composition is between 2% and 4%. In some embodiments, the total pilocarpine concentration in the composition is between 2% and 3%. In some embodiments, the total pilocarpine concentration in the composition is between 1% and 4%. In some embodiments, the total pilocarpine concentration in the composition is between 1% and 2%. In some embodiments, the total pilocarpine concentration in the composition is between 0.01% and 3%. In some embodiments, the total pilocarpine concentration in the composition is between 1% and 3%. In some embodiments, the total pilocarpine concentration in the composition is between 0.01% and 2%. In some embodiments, the total pilocarpine concentration in the composition is between 0.01% and 1%. In some embodiments, the total pilocarpine concentration in the composition is between 0.01% and 0.5%. In some embodiments, the total pilocarpine concentration in the composition is between 0.01% and 0.1%.

In some embodiments, the concentration of nicotine, or a salt thereof, in the composition is between 1 mg and 5 mg. In some embodiments, the composition comprises between 1 mg and 4 mg nicotine, or a salt thereof. In some embodiments, the composition comprises between 2 mg and 4 mg nicotine, or a salt thereof. In some embodiments, the composition comprises between 1 mg and 3 mg nicotine, or a salt thereof. In some embodiments, the composition comprises between 1 mg and 2 mg nicotine, or a salt thereof. In some embodiments, the composition comprises between 3 mg and 4 mg nicotine, or a salt thereof. In some embodiments, the composition comprises between 2 mg and 3 mg nicotine, or a salt thereof. In some embodiments, the composition comprises 1 mg nicotine, or a salt thereof. In some embodiments, the composition comprises 2 mg nicotine, or a salt thereof. In some embodiments, the composition comprises 3 mg nicotine, or a salt thereof. In some embodiments, the composition comprises 4 mg nicotine, or a salt thereof.

In another aspect, provided herein are pharmaceutical compositions comprising nicotine, or a salt thereof, and pilocarpine, or a salt thereof. Pharmaceutical compositions described herein can be prepared by any method known in the art of pharmacology. In general, such preparatory methods include bringing the compound described herein (i.e., the "active ingredient(s)" (e.g., pilocarpine, nicotine)) into association with a carrier or excipient, and/or one or more other accessory ingredients, and then, if necessary and/or desirable, shaping, and/or packaging the product into a desired single- or multi-dose unit. In some embodiments, the pharmaceutical composition comprises a pharmaceutically acceptable carrier, adjuvant, excipient, or buffer.

Relative amounts of the active ingredient(s) (e.g., pilocarpine, nicotine), the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.01% and 100% (w/w) active ingredient(s) (e.g., pilocarpine, nicotine).

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition. The exact amount of a composition required to achieve an effective amount will vary from subject to subject, depending, for example, on species, age, and general condition of a subject, severity of the side effects or disorder, identity of the particular compound, mode of administration, and the like. In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for preventing a disease. In certain embodiments, the effective amount is an amount effective for reducing the risk of developing cancer. In some embodiments, the cancer is oral, head and neck, lung, throat, or esophageal cancer. In certain embodiments, the effective amount is an amount effective for reducing the risk of developing a painful condition. In certain embodiments, the effective amount is an amount effective for alleviating withdrawal symptoms of an addiction. In some embodiments, the painful condition is pain associated with withdrawal symptoms of an addiction. In certain embodiments, the effective amount is an amount effective for reducing the risk of developing a neurological disease. In some embodiments, the neurological disease is an addiction. In some embodiments, the addiction is a tobacco, nicotine, betel quid, or areca nut addiction, or an addiction to a betel quid equivalent. In certain embodiments, the effective amount is an amount effective for reducing the risk of developing an oral disease. In some embodiments, the oral disease is periodontal disease, oral lesions, smokeless tobacco keratosis, leukoplakia, gingival recession, coronal decay, or root caries. In some embodiments, the effective amount is an amount effective for reducing betel quid use, or the use of a betel quid equivalent. In some embodiments, the effective amount is an amount effective for preventing betel quid use, or the use of a betel quid equivalent. In some embodiments, the effective amount is an amount effective for achieving betel quid, tobacco, or areca nut cessation.

An effective amount may be included in a single dose (e.g., single oral dose) or multiple doses (e.g., multiple oral doses). In certain embodiments, when multiple doses are administered to a subject, any two doses of the multiple doses include different or substantially the same amounts of a compound described herein. In certain embodiments, when multiple doses are administered to a subject, the frequency of administering the multiple doses to the subject is ten doses a day, nine doses a day, eight doses a day, seven doses a day, six doses a day, five doses a day, four doses a day, three doses a day, two doses a day, one dose a day, or one dose every other day. In certain embodiments, the frequency of administering the multiple doses to the subject is one dose per day. In certain embodiments, the frequency of administering the multiple doses to the subject is two doses per day. In certain embodiments, the frequency of administering the multiple doses to the subject is three doses per day. In certain embodiments, the frequency of administering the multiple doses to the subject is four doses per day. In certain embodiments, the frequency of administering the multiple doses to the subject is five doses per day. In certain embodiments, the frequency of administering the multiple doses to the subject is six doses per day. In certain embodiments, the frequency of administering the multiple doses to the subject is seven doses per day. In certain embodiments, the frequency of administering the multiple doses to the subject is eight doses per day. In certain embodiments, the frequency of administering the multiple doses to the subject is nine doses per day. In certain embodiments, the frequency of administering the multiple doses to the subject is ten doses per day. In certain embodiments, when multiple doses are administered to a subject or applied to a tissue or cell, the duration between the first dose and last dose of the multiple doses is one hour, two hours, three hours, four hours, five hours, six hours, seven hours, eight hours, nine hours, ten hours, eleven hours, twelve hours, one day, or two days. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, or between 30 mg and 100 mg, inclusive, of a composition described herein. In certain embodiments, a dose described herein includes independently between 1 mg and 5 mg, inclusive, of a composition described herein. In certain embodiments, a dose described herein includes independently between 5 mg and 10 mg, inclusive, of a composition described herein. In certain embodiments, a dose described herein includes independently between 1 mg and 2 mg, inclusive, of a composition described herein. In certain embodiments, a dose described herein includes independently between 2 mg and 4 mg, inclusive, of a composition described herein. In certain embodiments, a dose described herein includes independently between 4 mg and 6 mg, inclusive, of a composition described herein. In certain embodiments, a dose described herein includes independently between 6 mg and 8 mg, inclusive, of a composition described herein. In certain embodiments, a dose described herein includes independently between 8 mg and 10 mg, inclusive, of a composition described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is about 50 to about 80 kg.

Acceptable excipients used in the manufacture of provided compositions and pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In some embodiments, the composition or pharmaceutical composition thereof is formulated for oral administration.

In one aspect, provided herein is a composition comprising nicotine, or a salt thereof, pilocarpine, or a salt thereof, and optionally an acceptable carrier, adjuvant, excipient, or buffer for oral administration. In some embodiments, the composition consists essentially of nicotine, or a salt thereof, pilocarpine, or a salt thereof, and an acceptable carrier, adjuvant, excipient, or buffer for oral administration. In some embodiments, the composition consists of nicotine, or a salt thereof, pilocarpine, or a salt thereof, and an acceptable carrier, adjuvant, excipient, or buffer for oral administration.

Solid dosage forms for oral administration include capsules, tablets, pills, powders, and granules. In such solid dosage forms, the active ingredient(s) (e.g., pilocarpine, nicotine) is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient(s) (e.g., pilocarpine, nicotine) is mixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient(s) (e.g., pilocarpine, nicotine) to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

In some embodiments, the composition is prepared, packaged, sold, and/or administered as a chewing gum, lozenge, or tablet. In some embodiments, the composition is a chewing gum. In some embodiments, the gum comprises nicotine, or a salt thereof. In some embodiments, the gum comprises between 1 mg and 4 mg nicotine, or a salt thereof. In some embodiments, the gum comprises between 1 mg and 3 mg nicotine, or a salt thereof. In some embodiments, the gum comprises between 1 mg and 2 mg nicotine, or a salt thereof. In some embodiments, the gum comprises between 2 mg and 4 mg nicotine, or a salt thereof. In some embodiments, the gum comprises between 2 mg and 3 mg nicotine, or a salt thereof. In some embodiments, the gum comprises 1 mg nicotine, or a salt thereof. In some embodiments, the gum comprises 2 mg nicotine, or a salt thereof. In some embodiments, the gum comprises 4 mg nicotine, or a salt thereof. In some embodiments, the chewing gum comprises one or more sweeteners and/or flavoring agents. In general, sweeteners, which may or may not be perceptively "sweet," impart palatability to the chewing gum composition to improve tolerance and compliance. Sweeteners are often saccharides (e.g., mono-, di-, tri- and polysaccharide materials known in the art, including oligomers, and oligosaccharides. Non-limiting examples of sweeteners include sugars (e.g., sucrose, glucose, corn syrup, dextrose, invert sugar, fructose, and mixtures thereof. Examples of less or non-sweet sugars and polysaccharide material, such as maltodextrin and polydextrose, may also be utilized. "Sugar-free" or "non-sucrose" formulations may be desirable in certain embodiments. Thus, other sweeteners may be selected from the group consisting of saccharin, or salts thereof (e.g., sodium and calcium salts), cyclamic acid, or salts thereof, dipeptide sweeteners, chlorinated sugar derivatives (e.g., sucralose, dihydrochalcone, glycyrrhin, *Stevia rebaudiana* (Stevioside), and sugar alcohols (e.g., sorbitol, sorbitol syrup, mannitol, xylitol, hexa-resorcinol). Non-limiting examples of flavoring agents include peppermint, spearmint, wintergreen, cinnamon, menthol, and menthone flavors.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient(s) (e.g., pilocarpine, nicotine) may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient(s) (e.g., pilocarpine, nicotine) in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient(s) (e.g., pilocarpine, nicotine), and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient(s) (e.g., pilocarpine, nicotine), the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient(s) (e.g., pilocarpine, nicotine). Such powdered, aerosolized, and/or aerosolized formulations, when dispersed, may have an average particle and/or droplet size in the range from about 0.1 to about 200 nanometers, and may further comprise one or more of the additional ingredients described herein. Alternatively, formulations for buccal administration may be in the form of gum made using conventional methods (e.g., hot-melt extrusion), and may contain, for example, 0.1 to 20% (w/w) active ingredient(s) (e.g., pilocarpine, nicotine), the balance comprising a composition which does not dissolve and/or degrade upon chewing, and, optionally, one of more of the additional ingredients described herein.

The compositions provided herein can be administered by any route, including enteral (e.g., oral), parenteral, transdermal, intradermal, topical (as by powders, ointments, creams, and/or drops), mucosal, nasal, buccal, sublingual; by inhalation; and/or as an oral spray, nasal spray, and/or aerosol. In certain embodiments, the composition is administered by oral route, regionally administered via mucosal supply, and/or directly administration to an affected site (e.g., oral cavity). In general, the most appropriate route of administration will depend upon a variety of factors including the nature of the agent (e.g., its stability in the environment of the gastrointestinal tract), and/or the condition of the subject (e.g., whether the subject is able to tolerate oral administration).

A composition, as described herein, can be administered in combination with one or more additional pharmaceutical agents (e.g., therapeutically and/or prophylactically active agents). The composition can be administered in combination with additional pharmaceutical agents that improve the activity of the active ingredient(s) (e.g., pilocarpine, nicotine) (e.g., activity (e.g., potency and/or efficacy) in preventing a disease in a subject in need thereof, in reducing the risk to develop a disease in a subject in need thereof, and/or in alleviating withdrawal symptoms), improve bioavailability, improve safety, reduce drug resistance, reduce and/or modify metabolism, inhibit excretion, and/or modify distribution in a subject. In certain embodiments, a pharmaceutical composition described herein including a composition comprising active ingredients (e.g., pilocarpine, nicotine) described herein and an additional pharmaceutical agent shows a synergistic effect that is absent in a pharmaceutical composition including one of the composition and the additional pharmaceutical agent, but not both.

The compound or composition can be administered concurrently with, prior to, or subsequent to one or more additional therapeutic agents, which are different from the compound or composition and may be useful as, e.g., combination therapies. Pharmaceutical agents include therapeutically active agents. Pharmaceutical agents also include prophylactically active agents. Pharmaceutical agents include small organic molecules such as small molecule drug compounds (e.g., compounds approved for human or veterinary use by the U.S. Food and Drug Administration as provided in the Code of Federal Regulations (CFR)), carbohydrates, monosaccharides, oligosaccharides, polysaccharides, steroids, lipids, hormones, and vitamins. In certain embodiments, the additional pharmaceutical agent is a pharmaceutical agent useful for preventing a disease (e.g., cancer, oral disease, neurological disease, or painful condition). Each additional pharmaceutical agent may be administered at a dose and/or on a time schedule determined for that pharmaceutical agent. The additional pharmaceutical agents may also be administered together with each other and/or with the composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In some embodiments, the additional pharmaceutical agent is an anti-addiction agent, anti-smoking agent, anti-nicotine addiction agent, anti-betel addiction agent, anti-areca nut addiction agent, and the like. In some embodiments, the additional pharmaceutical agent is selected from Nicoderm CQ®, Zyban®, Nicotrol®, Nicorette® buccal, Nicotrol NS®, inhaled nicotine, buprorion HCl, NTS Step 1®, Stop Smoking Aid®, Nicorelief®, Quit 2®, and Quit 4®.

Also encompassed by the disclosure are kits (e.g., pharmaceutical packs). The kits provided may comprise a composition described herein and a container (e.g., a vial, ampule, bottle, syringe, and/or dispenser package, or other suitable container). In some embodiments, provided kits may include multiple doses of the composition in a dispenser pack comprising two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or more individual doses.

In certain embodiments, a kit described herein further includes instructions for using the kit. A kit described herein may also include information as required by a regulatory agency such as the U.S. Food and Drug Administration (FDA). In certain embodiments, the information included in the kits is prescribing and dosing information. In certain embodiments, the kits and instructions provide for preventing a disease (e.g., cancer, oral disease, neurological disease, or painful condition) in a subject in need thereof. In certain embodiments, the kits and instructions provide for reducing the risk of developing a disease (e.g., cancer, oral disease, neurological disease, or painful condition) in a subject in need thereof. In certain embodiments, the kits and instructions provide for alleviating withdrawal symptoms from an addiction (e.g., nicotine addiction, betel quid addiction, areca nut addiction, tobacco addition, etc.). A kit described herein may include one or more additional pharmaceutical agents described herein as a separate composition.

Methods of Making Compositions Comprising Nicotine and Pilocarpine

As shown in Example 1, oral formulations of compositions comprising pilocarpine, or a salt thereof, and nicotine, or a salt thereof, may be useful in many contexts, for example in reducing betel quid use, encouraging betel quid cessation, and preventing and/or reducing the risk of developing a disease (e.g., cancer, oral disease, neurological disease, or painful condition).

In one aspect, provided herein is a method of making a composition comprising nicotine, or a salt thereof, and pilocarpine, or a salt thereof. In some embodiments, the method comprises adding pilocarpine, or a salt thereof, to a formulation comprising nicotine, or a salt thereof, thereby producing a composition comprising nicotine and pilocarpine. In some embodiments, the method comprises adding nicotine, or a salt thereof, to a formulation comprising pilocarpine, or a salt thereof, thereby producing a composition comprising nicotine and pilocarpine. In some embodiments, the formulation is a liquid formulation (e.g., a solution comprising nicotine). In some embodiments, the formulation is a solid formulation (e.g., a powder, pill, capsule, gum, tablet, or other suitable solid formulation comprising nicotine). In some embodiments, the method comprises adding pilocarpine, or a salt thereof, to an oral formulation comprising nicotine, or a salt thereof, thereby producing a composition comprising nicotine and pilocarpine. In some embodiments, the composition further comprises an acceptable carrier, adjuvant, buffer, or excipient. In some embodiments, the method comprises adding pilocarpine, or a salt thereof, to an oral formulation comprising nicotine, or a salt thereof, thereby producing a composition comprising nicotine and pilocarpine. In some embodiments, the composition is administered to the subject by oral route. In some embodiments, the oral formulation is a chewing gum, spray, lozenge, or pouch product. In some embodiments, the oral formulation is a chewing gum.

In another aspect, provided herein is a method of making a pharmaceutical composition comprising nicotine, or a salt thereof, and pilocarpine, or a salt thereof. In some embodiments, the method comprises adding pilocarpine, or a salt thereof, to a formulation comprising nicotine, or a salt thereof, thereby producing a pharmaceutical composition comprising nicotine and pilocarpine. In some embodiments, the method comprises adding nicotine, or a salt thereof, to a formulation comprising pilocarpine, or a salt thereof, thereby producing a pharmaceutical composition comprising nicotine and pilocarpine. In some embodiments, the formulation is a liquid formulation (e.g., a solution comprising nicotine). In some embodiments, the formulation is a solid formulation (e.g., a powder, pill, capsule, gum, tablet, or other suitable solid formulation comprising nicotine). In some embodiments, the method comprises adding pilocarpine, or a salt thereof, to an oral formulation comprising nicotine, or a salt thereof, thereby producing a composition comprising nicotine and pilocarpine. In some embodiments, the composition further comprises a pharmaceutically acceptable carrier, adjuvant, buffer, or excipient. In some embodiments, the method comprises adding pilocarpine, or a salt thereof, to an oral formulation comprising nicotine, or a salt thereof, thereby producing a composition comprising nicotine and pilocarpine. In some embodiments, the composition is administered to the subject by oral route. In some embodiments, the oral formulation is a chewing gum, spray, lozenge, or pouch product. In some embodiments, the oral formulation is a chewing gum.

In some embodiments, the oral formulation is produced using hot-melt extrusion, thus providing a hot-melt extrusion product comprising nicotine, pilocarpine, or a combination thereof. In some embodiments, the hot-melt extrusion product comprises nicotine, and pilocarpine is subsequently added to the hot-melt extrusion product, thus forming a composition comprising, consisting essentially of, or consisting of nicotine and pilocarpine. In some embodiments, the hot melt-extrusion product comprises pilocarpine, and nicotine is subsequently added to the hot-melt extrusion product, thus forming a composition comprising, consisting essentially of, or consisting of nicotine and pilocarpine. In some embodiments, the hot-melt extrusion product comprises nicotine and pilocarpine, thus providing a composition comprising, consisting essentially of, or consisting of nicotine and pilocarpine. In some embodiments, the hot-melt extrusion product comprises a gum base. Hot-melt extrusion processes for the preparation of compositions, including pharmaceutical compositions, is known in the art (see, e.g., Maniruzzaman M et al. (2012) A Review of Hot-Melt Extrusion: Process Technology to Pharmaceutical Products. *ISRN Pharmaceuticals* (doi:10.5402/2012/436763), which is herein incorporated by reference). The appropriate hot-melt extrusion process will be chosen by a person of ordinary skill in the art based on the desired consistency, dosage regimen, active ingredients (e.g., pilocarpine, nicotine), additional therapeutic agents, and/or additional ingredients (e.g., flavoring agents, etc.).

In some embodiments, pilocarpine, or a salt thereof, is added to a formulation. In some embodiments, the formulation is a liquid formulation (e.g., a solution). In some embodiments, the formulation is a solid formulation (e.g., a powder or tablet). In some embodiments, pilocarpine, or a salt thereof, is added to a formulation comprising nicotine, or a salt thereof, thereby producing a composition or a pharmaceutical composition comprising nicotine and pilocarpine. In some embodiments, the pilocarpine is added in a liquid form of pilocarpine, or a salt thereof. In some embodiments, the liquid pilocarpine is a solution of pilocarpine hydrochloride. In some embodiments, the pilocarpine solution comprises between about 1% and about 10% pilocarpine hydrochloride. In some embodiments, the pilocarpine solution is a 1% pilocarpine hydrochloride solution. In some embodiments, the pilocarpine solution is a 2% pilocarpine hydrochloride solution. In some embodiments, the pilocarpine solution is a 3% pilocarpine hydrochloride solution. In some embodiments, the pilocarpine solution is a 4% pilocarpine hydrochloride solution. In some embodiments, the pilocarpine solution is a 5% pilocarpine hydrochloride solution. In some embodiments, the pilocarpine solution is a 6% pilocarpine hydrochloride solution. In some embodiments, the pilocarpine solution is a 7% pilocarpine hydrochloride solution. In some embodiments, the pilocarpine solution is a 8% pilocarpine hydrochloride solution. In some embodiments, the pilocarpine solution is a 9% pilocarpine hydrochloride solution. In some embodiments, the pilocarpine solution is a 10% pilocarpine hydrochloride solution. In some embodiments, the pilocarpine solution is a 1%, 2%, or 4% pilocarpine hydrochloride solution.

In some embodiments, between about 1 L and about 10 L of the pilocarpine solution are added to the formulation. In some embodiments, between about 1 L and about 5 L of the pilocarpine solution are added to the formulation. In some embodiments, between about 5 L and about 10 L of the pilocarpine solution are added to the formulation. In some embodiments, between about 1 mL and about 1 L of the pilocarpine solution are added to the formulation. In some embodiments, between about 1 mL and about 500 mL of the pilocarpine solution are added to the formulation. In some embodiments, between about 1 mL and about 100 mL of the pilocarpine solution are added to the formulation. In some embodiments, between about 1 mL and about 10 mL of the pilocarpine solution are added to the formulation. In some embodiments, between about 0.1 mL and about 10 mL of the pilocarpine solution are added to the formulation. In some embodiments, between about 0.1 mL and about 5 mL of the pilocarpine solution are added to the formulation. In some embodiments, between about 0.1 mL and about 4 mL of the pilocarpine solution are added to the formulation. In some embodiments, between about 0.1 mL and about 3 mL of the pilocarpine solution are added to the formulation. In some embodiments, between about 0.1 mL and about 2 mL of the pilocarpine solution are added to the formulation. In some embodiments, between about 0.1 mL and about 1 mL of the pilocarpine solution are added to the formulation. In some embodiments, between about 0.1 mL and about 0.5 mL of the pilocarpine solution are added to the formulation. In some embodiments, between about 5 mL and about 10 mL of the pilocarpine solution are added to the formulation. In some embodiments, between about 5 mL and about 9 mL of the pilocarpine solution are added to the formulation. In some embodiments, between about 5 mL and about 8 mL of the pilocarpine solution are added to the formulation. In some embodiments, between about 5 mL and about 7 mL of the pilocarpine solution are added to the formulation. In some embodiments, between about 5 mL and about 6 mL of the pilocarpine solution are added to the formulation. In some embodiments, 0.5 mL of the pilocarpine solution is added to the formulation. In some embodiments, 1 mL of the pilocarpine solution is added to the formulation. In some embodiments, 1.5 mL of the pilocarpine solution is added to the formulation. In some embodiments, 2 mL of the pilocarpine solution is added to the formulation. In some embodiments, 2.5 mL of the pilocarpine solution is added to the formulation. In some embodiments, 3 mL of the pilocarpine solution is added to the formulation. In some embodiments, 3.5 mL of the pilocarpine solution is added to the formulation. In some embodiments, 4 mL of the pilocarpine solution is added to the formulation. In some embodiments, 4.5 mL of the pilocarpine solution is added to the formulation. In some embodiments, 5 mL of the pilocarpine solution is added to the formulation. In some embodiments, the formulation comprises nicotine, or a salt thereof. In some embodiments, the formulation is a hot-melt extrusion product. In some embodiments, the formulation is a gum, lozenge, spray, or pouch product. In some embodiments, the formulation is gum.

In some embodiments, pilocarpine, or a salt thereof, is added to an oral formulation. In some embodiments, pilocarpine, or a salt thereof, is added to an oral formulation comprising nicotine, or a salt thereof, thereby producing a composition or a pharmaceutical composition comprising nicotine and pilocarpine. In some embodiments, the pilocarpine is added in a liquid form of pilocarpine, or a salt thereof. In some embodiments, the liquid pilocarpine is a solution of pilocarpine hydrochloride. In some embodiments, the pilocarpine solution comprises between about 1% and about 10% pilocarpine hydrochloride. In some embodiments, the pilocarpine solution is a 1% pilocarpine hydrochloride solution. In some embodiments, the pilocarpine solution is a 2% pilocarpine hydrochloride solution. In some embodiments, the pilocarpine solution is a 3% pilocarpine hydrochloride solution. In some embodiments, the pilocarpine solution is a 4% pilocarpine hydrochloride solution. In some embodiments, the pilocarpine solution is a 5% pilocarpine hydrochloride solution. In some embodiments, the pilocarpine solution is a 6% pilocarpine hydrochloride solution. In some embodiments, the pilocarpine solution is a 7% pilocarpine hydrochloride solution. In some embodiments, the pilocarpine solution is a 8% pilocarpine hydrochloride solution. In some embodiments, the pilocarpine solution is a 9% pilocarpine hydrochloride solution. In some embodiments, the pilocarpine solution is a 10% pilocarpine hydrochloride solution. In some embodiments, the pilocarpine solution is a 1%, 2%, or 4% pilocarpine hydrochloride solution.

In some embodiments, between about 1 L and about 10 L of the pilocarpine solution are added to the oral formulation. In some embodiments, between about 1 L and about 5 L of the pilocarpine solution are added to the oral formulation. In some embodiments, between about 5 L and about 10 L of the pilocarpine solution are added to the oral formulation. In some embodiments, between about 1 mL and about 1 L of the pilocarpine solution are added to the oral formulation. In some embodiments, between about 1 mL and about 500 mL of the pilocarpine solution are added to the oral formulation. In some embodiments, between about 1 mL and about 100 mL of the pilocarpine solution are added to the oral formulation. In some embodiments, between about 1 mL and about 10 mL of the pilocarpine solution are added to the oral formulation. In some embodiments, between about 0.1 mL and about 10 mL of the pilocarpine solution are added to the oral formulation. In some embodiments, between about 0.1 mL and about 5 mL of the pilocarpine solution are added to the oral formulation. In some embodiments, between about 0.1 mL and about 4 mL of the pilocarpine solution are added to the oral formulation. In some embodiments, between about 0.1 mL and about 3 mL of the pilocarpine solution are added to the oral formulation. In some embodiments, between about 0.1 mL and about 2 mL of the pilocarpine solution are added to the oral formulation. In some embodiments, between about 0.1 mL and about 1 mL of the pilocarpine solution are added to the oral formulation. In some embodiments, between about 0.1 mL and about 0.5 mL of the pilocarpine solution are added to the oral formulation. In some embodiments, between about 5 mL and about 10 mL of the pilocarpine solution are added to the oral formulation. In some embodiments, between about 5 mL and about 9 mL of the pilocarpine solution are added to the oral formulation. In some embodiments, between about 5 mL and about 8 mL of the pilocarpine solution are added to the oral formulation. In some embodiments, between about 5 mL and about 7 mL of the pilocarpine solution are added to the oral formulation. In some embodiments, between about 5 mL and about 6 mL of the pilocarpine solution are added to the oral formulation. In some embodiments, 0.5 mL of the pilocarpine solution is added to the oral formulation. In some embodiments, 1 mL of the pilocarpine solution is added to the oral formulation. In some embodiments, 1.5 mL of the pilocarpine solution is added to the oral formulation. In some embodiments, 2 mL of the pilocarpine solution is added to the oral formulation. In some embodiments, 2.5 mL of the pilocarpine solution is added to the oral formulation. In some embodiments, 3 mL of the pilocarpine solution is added to the oral formulation. In some embodiments, 3.5 mL of the pilocarpine solution is added to the oral formulation. In some embodiments, 4 mL of the pilocarpine solution is added to the oral formulation. In some embodiments, 4.5 mL of the pilocarpine solution is added to the oral formulation. In some embodiments, 5 mL of the pilocarpine solution is added to the oral formulation. In some embodiments, the oral formulation comprises nicotine, or a salt thereof. In some embodiments, the oral formulation is a hot-melt extrusion product. In some embodiments, the oral formulation is a gum, lozenge, spray, or pouch product. In some embodiments, the oral formulation is gum.

In some embodiments, pilocarpine, or a salt thereof, is added to an oral formulation. In some embodiments, pilocarpine, or a salt thereof, is added to an oral formulation comprising nicotine, or a salt thereof, thereby producing a composition or a pharmaceutical composition comprising nicotine and pilocarpine. In some embodiments, the pilocarpine is added in a solid form of pilocarpine, or a salt thereof. In some embodiments, the pilocarpine added is a powder comprising pilocarpine, or a salt thereof.

In some embodiments, between about 1 g and about 1 kg of the powder comprising pilocarpine, or a salt thereof, are added to the oral formulation. In some embodiments, between about 1 g and about 10 g of the powder comprising pilocarpine, or a salt thereof, are added to the oral formulation. In some embodiments, between about 1 g and about 5 g of the powder comprising pilocarpine, or a salt thereof, are added to the oral formulation. In some embodiments, between about 5 g and about 10 g of the powder comprising pilocarpine, or a salt thereof, are added to the oral formulation. In some embodiments, between about 1 mg and about 1 g of the powder comprising pilocarpine, or a salt thereof, are added to the oral formulation. In some embodiments, between about 1 mg and about 500 mg of the powder comprising pilocarpine, or a salt thereof, are added to the oral formulation. In some embodiments, between about 1 mg and about 100 mg of the powder comprising pilocarpine, or a salt thereof, are added to the oral formulation. In some embodiments, between about 1 mg and about 10 mg of the powder comprising pilocarpine, or a salt thereof, are added to the oral formulation. In some embodiments, between about 0.1 mg and about 10 mg of the powder comprising pilocarpine, or a salt thereof, are added to the oral formulation. In some embodiments, between about 0.1 mg and about 5 mg of the powder comprising pilocarpine, or a salt thereof, are added to the oral formulation. In some embodiments, between about 0.1 mg and about 4 mg of the powder comprising pilocarpine, or a salt thereof, are added to the oral formulation. In some embodiments, between about 0.1 mg and about 3 mg of the powder comprising pilocarpine, or a salt thereof, are added to the oral formulation. In some embodiments, between about 0.1 mg and about 2 mg of the powder comprising pilocarpine, or a salt thereof, are added to the oral formulation. In some embodiments, between about 0.1 mg and about 1 mg of the powder comprising pilocarpine, or a salt thereof, are added to the oral formulation. In some embodiments, between about 0.1 mg and about 0.5 mg of the powder comprising pilocarpine, or a salt thereof, are added to the oral formulation. In some embodiments, between about 5 mg and about 10 mg of the powder comprising pilocarpine, or a salt thereof, are added to the oral formulation. In some embodiments, between about 5 mg and about 9 mg of the powder comprising pilocarpine, or a salt thereof, are added to the oral formulation. In some embodiments, between about 5 mg and about 8 mg of the powder comprising pilocarpine, or a salt thereof, are added to the oral formulation. In some embodiments, between about 5 mg and about 7 mg of the powder comprising pilocarpine, or a salt thereof, are added to the oral formulation. In some embodiments, between about 5 mg and about 6 mg of the powder comprising pilocarpine, or a salt thereof, are added to the oral formulation. In some embodiments, 1 mg of the powder comprising pilocarpine, or a salt thereof, are added to the oral formulation. In some embodiments, 1 g of the powder comprising pilocarpine, or a salt thereof, are added to the oral formulation. In some embodiments, the oral formulation comprises nicotine, or a salt thereof. In some embodiments, the oral formulation is a hot-melt extrusion product. In some embodiments, the oral formulation is a gum, lozenge, spray, or pouch product. In some embodiments, the oral formulation is gum.

In some embodiments, nicotine, or a salt thereof, is added to a formulation. In some embodiments, the formulation is a liquid formulation (e.g., a solution). In some embodiments, the formulation is a solid formulation (e.g., a powder or tablet). In some embodiments, nicotine, or a salt thereof, is added to a formulation comprising pilocarpine, or a salt thereof, thereby producing a composition or a pharmaceutical composition comprising nicotine and pilocarpine.

Methods of Use

As discussed above, compositions comprising nicotine and pilocarpine provide a safer alternative (e.g., replacement therapy) for subjects who routinely use and/or are addicted to betel quid and/or areca nut. For example, without wishing to be bound by any particular theory, subjects who use (e.g., chew) betel quid, or an equivalent preparation, may find using an orally administered composition (e.g., chewing gum) comprising pilocarpine and nicotine to be an effective replacement therapy for betel quid, as shown in Example 1. In addition, the compositions described herein may prevent subjects from using or reduce the frequency of using betel quid and/or areca nut, thus serving as a preventative measure against the development or further progression of one or more diseases (e.g., cancer, oral disease, neurological disease, or painful condition).

In one aspect, provided herein is a method of reducing the risk of developing a disease, the method comprising administering to a subject in need thereof an effective amount of a composition or pharmaceutical composition described herein. In some embodiments, the risk of developing a disease is reduced in a subject who has used (e.g., chews) betel quid one or more times and/or is addicted to betel quid, or an equivalent preparation. In some embodiments, the composition or pharmaceutical composition is administered to the subject before the disease has developed (e.g., prophylactic treatment of the disease). In some embodiments, the composition or pharmaceutical composition is administered to the subject before the disease has substantially progressed. "Substantially progressed" is intended to describe a disease that is not yet fully developed. In some embodiments, the disease, or symptoms thereof, is associated with stimulation of nicotinic acetylcholinergic receptors (nAChRs), stimulation of muscarinic acetylcholinergic receptors (mAChRs), or stimulation of both nAChRs and mAChRs. In some embodiments, the disease is Alzheimer's disease, Parkinson's disease, schizophrenia, Tourette's syndrome, anxiety, depression, epilepsy, chronic obstructive pulmonary disease (COPD), or motion sickness. In some embodiments, the disease is cancer. In some embodiments, the cancer is oral cancer, throat cancer, esophageal cancer, head and neck cancer, or lung cancer. In some embodiments, the disease is an oral disease. In some embodiments, the oral disease comprises periodontal disease, oral lesions, smokeless tobacco keratosis, leukoplakia, gingival recession, coronal decay, or root caries. In some embodiments, the oral disease is periodontal disease, oral lesions, smokeless tobacco keratosis, leukoplakia, gingival recession, coronal decay, or root caries. In some embodiments, the disease is a neurological disease. In some embodiments, the neurological disease is an addiction. In some embodiments, the addiction is a betel quid addiction, or an addiction to an equivalent preparation. In some embodiments, the addiction is an areca nut addiction. In some embodiments, the addiction is a nicotine addiction. In some embodiments, the disease is a painful condition. In some embodiments, the painful condition is pain associated with withdrawal symptoms from an addiction. In some embodiments, the addiction is a betel quid addiction, or an addiction to an equivalent preparation. In some embodiments, the addiction is an areca nut addiction. In some embodiments, the addiction is a nicotine addiction. In some embodiments, the effective amount is a therapeutically effective amount or a prophylactically effective amount. In some embodiments, the composition or pharmaceutical composition is administered orally.

In another aspect, provided herein is a method of reducing the progression of a disease, the method comprising administering to a subject in need thereof an effective amount of a composition or pharmaceutical composition described herein. In some embodiments, the composition or pharmaceutical composition is administered to the subject before the disease has substantially progressed. "Substantially progressed" is intended to describe a disease that is not yet fully developed. In some embodiments, the composition or pharmaceutical composition is administered to the subject after the disease has substantially progressed (e.g., after the disease has fully developed). In some embodiments, the disease, or symptoms thereof, is associated with stimulation of nicotinic acetylcholinergic receptors (nAChRs), stimulation of muscarinic acetylcholinergic receptors (mAChRs), or stimulation of both nAChRs and mAChRs. In some embodiments, the disease is Alzheimer's disease, Parkinson's disease, schizophrenia, Tourette's syndrome, anxiety, depression, epilepsy, chronic obstructive pulmonary disease (COPD), or motion sickness. In some embodiments, the disease is cancer. In some embodiments, the cancer is oral cancer, throat cancer, esophageal cancer, head and neck cancer, or lung cancer. In some embodiments, the disease is an oral disease. In some embodiments, the oral disease comprises periodontal disease, oral lesions, smokeless tobacco keratosis, leukoplakia, gingival recession, coronal decay, or root caries. In some embodiments, the oral disease is periodontal disease, oral lesions, smokeless tobacco keratosis, leukoplakia, gingival recession, coronal decay, or root caries. In some embodiments, the disease is a neurological disease. In some embodiments, the neurological disease is an addiction. In some embodiments, the addiction is a betel quid addiction, or an addiction to an equivalent preparation. In some embodiments, the addiction is an areca nut addiction. In some embodiments, the addiction is a nicotine addiction. In some embodiments, the disease is a painful condition. In some embodiments, the painful condition is pain associated with withdrawal symptoms from an addiction. In some embodiments, the addiction is a betel quid addiction, or an addiction to an equivalent preparation. In some embodiments, the addiction is an areca nut addiction. In some embodiments, the addiction is a nicotine addiction. In some embodiments, the effective amount is a therapeutically effective amount or a prophylactically effective amount. In some embodiments, the composition or pharmaceutical composition is administered orally.

In yet another aspect, provided herein is a method for reducing betel quid and/or areca nut use, or use of an equivalent preparation, the method comprising administering to a subject in need thereof an effective amount of a composition or pharmaceutical composition described herein. In some embodiments, the subject uses betel quid and/or areca nut in the form of smokeless or chewing betel quid, or an equivalent preparation. In some embodiments, the subject also uses tobacco, betel leaves, roots, stems, or seeds, areca nut, slacked lime, or a combination thereof. In some embodiments, the frequency of betel quid and/or areca nut use is reduced upon administration of the composition or pharmaceutical composition. In some embodiments, the subject uses betel quid and/or areca nut, or an equivalent preparation, one less time upon administration of the composition or pharmaceutical composition. In some embodiments, the subject uses betel quid and/or areca nut, or an equivalent preparation, one less time upon administration of one or more doses of the composition or pharmaceutical composition. In some embodiments, the subject uses betel quid and/or areca nut, or an equivalent preparation, one less time over the course of a time period of about 24 hours (i.e., one day) upon administration of one or more doses of the composition or pharmaceutical composition. In some embodiments, the subject uses betel quid and/or areca nut, or an equivalent preparation, two, three, four, five, six, seven, eight, nine, ten, eleven, or twelve fewer times upon administration of one or more doses of the composition or pharmaceutical composition. In some embodiments, the subject uses betel quid and/or areca nut, or an equivalent preparation, two, three, four, five, six, seven, eight, nine, ten, eleven, or twelve fewer times over the course of a time period of about 24 hours (i.e., one day) upon administration of one or more doses of the composition or pharmaceutical composition. In some embodiments, reduction in betel quid and/or areca nut use, or use of an equivalent preparation, is achieved upon administration of one dose of the composition or pharmaceutical composition over the course of a time period of about 24 hours (i.e., one day). In some embodiments, reduction in betel quid and/or areca nut use, or use of an equivalent preparation, is achieved upon administration of more than one dose of the composition or pharmaceutical composition over the course of a time period of about 24 hours (i.e., one day). In some embodiments, reduction in betel quid and/or areca nut use, or use of an equivalent preparation, is achieved upon two, three, four, five, six, seven, eight, nine, ten, eleven, twelve, or more doses of the composition or pharmaceutical composition over the course of a time period of about 24 hours (i.e., one day). In some embodiments, the composition or pharmaceutical composition is administered orally.

In yet another aspect, provided herein is a method for achieving cessation of betel quid and/or areca nut use, or use of an equivalent preparation, the method comprising administering to a subject in need thereof an effective amount of a composition or pharmaceutical composition described herein. In some embodiments, the subject uses betel quid and/or areca nut in the form of smokeless or chewing betel quid, or an equivalent preparation. In some embodiments, the subject also uses tobacco, betel leaves, roots, stems, or seeds, areca nut, slacked lime, or a combination thereof. In some embodiments, cessation of betel quid and/or areca nut use, or the use of an equivalent preparation, is achieved upon administration of one or more doses of the composition or pharmaceutical composition. In some embodiments, cessation of betel quid and/or areca nut use, or the use of an equivalent preparation, is achieved upon administration of one or more doses of the composition or pharmaceutical composition over the course of about 24 hours (i.e., one day). In some embodiments, cessation of betel quid and/or areca nut use, or the use of an equivalent preparation, is achieved upon administration of one dose of the composition or pharmaceutical composition per day. In some embodiments, cessation of betel quid and/or areca nut use, or the use of an equivalent preparation, is achieved upon administration of two, three, four, five, six, seven, eight, nine, ten, eleven, twelve, or more doses of the composition or pharmaceutical composition per day. In some embodiments, cessation of betel quid and/or areca nut use, or the use of an equivalent preparation, is achieved upon administration of one or more doses of the composition or pharmaceutical composition over the course of about 48 hours (i.e., two days). In some embodiments, cessation of betel quid and/or areca nut use, or the use of an equivalent preparation, is achieved upon administration of one or more doses of the composition or pharmaceutical composition over the course of about 72 hours (i.e., three days). In some embodiments, cessation of betel quid and/or areca nut use, or the use of an equivalent preparation, is achieved upon administration of one or more doses of the composition or pharmaceutical composition over the course of about one week. In some embodiments, cessation of betel quid and/or areca nut use, or the use of an equivalent preparation, is achieved upon administration of one or more doses of the composition or pharmaceutical composition over the course of about two weeks. In some embodiments, the composition or pharmaceutical composition is administered orally.

In yet another aspect, provided herein is a method for eliminating withdrawal symptoms due to cessation of betel quid and/or areca nut use, or use of an equivalent preparation, the method comprising administering to a subject in need thereof an effective amount of a composition or pharmaceutical composition described herein. In some embodiments, the subject uses betel quid and/or areca nut in the form of smokeless or chewing betel quid, or an equivalent preparation. In some embodiments, the subject also uses tobacco, betel leaves, roots, stems, or seeds, areca nut, slacked lime, or a combination thereof. In some embodiments, the subject has attempted one or more nicotine-replacement therapies. "Nicotine-replacement therapy" comprises administration of one or more compounds or compositions that provide ease of symptoms (e.g., cravings) of withdrawal from nicotine or compositions comprising nicotine (e.g., tobacco). Common nicotine replacement therapies are nicotine gum or lozenges (e.g., Nicorette®, Thrive®, Commit®, Nicotex®, Habitrol®, etc.) or nicotine patches (e.g., NicoDerm CQ®). In some embodiments, withdrawal symptoms are eliminated upon administration of one or more doses of the composition or pharmaceutical composition. In some embodiments, withdrawal symptoms are eliminated upon administration of one or more doses of the composition or pharmaceutical composition over a time period of about 24 hours (i.e., one day). In some embodiments, withdrawal symptoms are eliminated upon administration of one dose of the composition or pharmaceutical composition per day. In some embodiments, withdrawal symptoms are eliminated upon administration of multiple doses of the composition or pharmaceutical composition per day. In some embodiments, withdrawal symptoms are eliminated upon administration of two, three, four, five, six, seven, eight, nine, ten, eleven, twelve, or more doses of the composition or pharmaceutical composition per day. In some embodiments, withdrawal symptoms are eliminated upon administration of one or more doses of the composition or pharmaceutical composition over a time period of about 48 hours (i.e., two days). In some embodiments, withdrawal symptoms are eliminated upon administration of one or more doses of the composition or pharmaceutical composition over a time period of about 72 hours (i.e., three days). In some embodiments, withdrawal symptoms are eliminated upon administration of one or more doses of the composition or pharmaceutical composition over a time period of about one week.

In yet another aspect, provided herein is a method for reducing the severity of withdrawal symptoms due to cessation of betel quid and/or areca nut use, or use of an equivalent preparation, the method comprising administering to a subject in need thereof an effective amount of a composition or pharmaceutical composition described herein. In some embodiments, the subject uses betel quid and/or areca nut in the form of smokeless or chewing betel quid, or an equivalent preparation. In some embodiments, the subject also uses tobacco, betel leaves, roots, stems, or seeds, areca nut, slacked lime, or a combination thereof. In some embodiments, the subject has attempted one or more nicotine-replacement therapies. In some embodiments, the severity of withdrawal symptoms are reduced upon administration of one or more doses of the composition or pharmaceutical composition. In some embodiments, the severity of withdrawal symptoms are reduced upon administration of one or more doses of the composition or pharmaceutical composition over a time period of about 24 hours (i.e., one day). In some embodiments, the severity of withdrawal symptoms are reduced upon administration of one dose of the composition or pharmaceutical composition per day. In some embodiments, the severity of withdrawal symptoms are reduced upon administration of multiple doses of the composition or pharmaceutical composition per day. In some embodiments, the severity of withdrawal symptoms are reduced upon administration of two, three, four, five, six, seven, eight, nine, ten, eleven, twelve, or more doses of the composition or pharmaceutical composition per day. In some embodiments, the severity of withdrawal symptoms are reduced upon administration of one or more doses of the composition or pharmaceutical composition over a time period of about 48 hours (i.e., two days). In some embodiments, the severity of withdrawal symptoms are reduced upon administration of one or more doses of the composition or pharmaceutical composition over a time period of about 72 hours (i.e., three days). In some embodiments, the severity of withdrawal symptoms are reduced upon administration of one or more doses of the composition or pharmaceutical composition over a time period of about one week.

EXAMPLES

In order that the invention described herein may be more fully understood, the following examples are set forth. The examples described in this application are offered to illustrate the methods, compositions, and systems provided herein and are not to be construed in any way as limiting their scope.

Example 1—Betel Quid Replacement Therapy

Study participants who regularly use and/or are addicted to betel quid, or a component within betel quid (e.g., areca nut), were recruited to take part in a focus group to test two products that could be used as substitutes for betel quid. All six chewers taking part in this focus group were males between the ages of 18 and 40 years old, with no known or reported health problems. Initially, chewers completed a questionnaire regarding their betel chewing habits. The two test products were then explained to the test subjects, and the subjects completed pre-treatment questionnaires, including whether or not the subject had any health problems that may cause a negative reaction to the test products.

All test subjects were given one piece of nicotine gum (2 mg nicotine, produced by Millimed, Thailand). Test subjects were required to chew this first test product for 3 minutes, followed by completion of a questionnaire (Table 1).

TABLE 1

| Nicotine gum (2 mg nicotine) | | | | | |
|---|---|---|---|---|---|
| Participant No. | a. Do you like chewing gum? | b. How often do you chew gum? | c. Do you like the flavour of this gum? | d. What do you feel when you chew this gum? | e. Does this gum feel similar to chewing betel? |
| 1 | Yes | Sometimes | Yes | Hot feeling in the mouth | No |
| 2 | Yes | Sometimes | It is not bad | Mint | No |
| 3 | Yes | Sometimes | No | Very hot feeling in the mouth | No |
| 4 | Yes | Sometimes | No | Dizzy | No |
| 5 | Yes | Sometimes, when I do not have any betel. | It is sweet | Dizzy | No |
| 6 | Yes | Sometimes | No | Hot and spicy feeling in the mouth | No |

| f. Do you think you could chew this gum every day and reduce chewing betel? | g. Would you chew this gum regularly instead of chewing betel? | h. How many pieces of this gum would you like to chew per day? | i. What do you like the most about this gum? | j. What do you like the least about this gum? | k. What would you like to change about this gum? |
|---|---|---|---|---|---|
| Yes | Yes | 5 pieces | Nothing | Hot feeling in the mouth | I would prefer it without the hot and spicy feeling in the mouth |
| I do not think so | No | None for me, but it should be about 3 to 4 pieces per day | Nothing | A little bit dizzy | Do not know |
| I do not think so | No | 5 pieces | The flavour | Salivation while chewing | It should have mint flavour |
| I do not think so | No | 0 pieces, I do not want to chew it | Chewing | Salivation while chewing | It should have mine flavour |

TABLE 1-continued

| | | Nicotine gum (2 mg nicotine) | | | |
|---|---|---|---|---|---|
| No | Yes, if the effect will be good | 6 pieces | Mint flavour | Dizzy feeling | Dizzy effect should be removed |
| Yes | Yes | 3 pieces | Nothing | Salivation while chewing | It should have (sweet) strawberry flavour |

Study participants were then given the same nicotine gum, but with the addition of one drop of pilocarpine solution (Piloptic-2) inserted into a small crater made in the center of the nicotine gum. Participants were asked to chew this second gum product for 3 minutes, and then complete a questionnaire (Table 2).

duced". Four out of six of the study participants are keen to continue using this pilocarpine-nicotine gum product, but were concerned about the flavour and requested flavour improvements, as well as improvements to the size of the product, since betel is typically larger than a single piece of gum. Overall, there is a clear need for an alternative product

TABLE 2

| | | | Nicotine gum (2 mg nicotine) + 1 drop pilocarpine (Piloptic-2) | | | | |
|---|---|---|---|---|---|---|---|
| Participant No. | a. Do you like the flavour of this gum? | b. What do you feel when you chew this gum? | c. Does this gum feel similar to chewing betel? | d. Do you think you could chew this gum every day and reduce chewing betel? | e. Would you chew this gum regularly instead of chewing betel? | f. How many pieces of this gum would you like to chew per day? | g. What do you like the most about this gum? |
| 1 | Yes | A little dizzy from the earlier gum | No | Yes | Yes | 10 pieces | Feeling is better than the first gum |
| 2 | Yes | Mint flavour | Yes | No, I think about chewing betel although I use this | I would chew this product and betel | 3 pieces | The flavour |
| 3 | Yes | Mint flavour | No | Yes | I do not think so | 5 pieces | The flavour |
| 4 | Yes | Chewing the product is the same as chewing betel | No | Yes | Low possibility (because of the size, much smaller than betel) | 8 pieces | Not a strong mint flavour |
| 5 | Yes | A little dizzy from the earlier gum | No | Maybe sometimes | Yes | 6 pieces | It is like chewing normal gum |
| 6 | Yes | Lots of saliva produced, similar to betel chewing | No | Yes | Yes | 3 pieces | Sweet flavour |

| h. What do you like the least about this gum? | i. What would you like to change about this gum? | j. Would you be willing sometimes to chew this gum instead of your Areca product, especially if you thought it might eventually help you quit using Areca? | k. Do you think the effects of the pilocarpine were: too high, not high enough, or just about right? | l. What additional flavour(s) do you think should be added to this gum? |
|---|---|---|---|---|
| Nothing | The size should be bigger than this. | Yes | Just about right | Piper betel leaf, sweetener |
| Nothing | All OK | Yes | Not high enough | Piper betel leaf, sweetener |
| Nothing | I want to change the mint flavour to sweet flavour | Yes | Just about right | Piper betel leaf |
| Nothing | The size should be bigger than this | Yes | Just about right | Piper betel leaf, cardamom seed |
| A little dizzy feeling | Dizzy effect should be removed | Yes | Just about right | Piper betel leaf, cardamom seed |
| Nothing | All OK | Yes | Not high enough | Sweetener, strawberry flavour |

All study participants reported wanting to quit betel quid. However, as shown in Table 1, the respondents did not like the first gum product (i.e., nicotine gum only) and reported feeling dizzy upon chewing the gum. In contrast, the respondents liked the addition of pilocarpine to the nicotine gum (test product two, as shown in Table 2) and reported that "it feels like chewing betel" because "lots of saliva [is] produced", so that betel quid users will be discouraged from using the addictive product, or potentially even stop using betel products altogether.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims. Where the claims or description relate to a product (e.g., a composition of matter), it should be understood that methods of making or using the product according to any of the methods disclosed herein, and methods of using the product for any one or more of the purposes disclosed herein, are encompassed by the present disclosure, where applicable, unless otherwise indicated or unless it would be evident to one of ordinary skill in the art that a contradiction or inconsistency would arise. Where the claims or description relate to a method, it should be understood that product(s), e.g., compositions of matter, device(s), or system(s), useful for performing one or more steps of the method are encompassed by the present disclosure, where applicable, unless otherwise indicated or unless it would be evident to one of ordinary skill in the art that a contradiction or inconsistency would arise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

What is claimed is:

1. A composition consisting of nicotine, or a salt thereof, pilocarpine, or a salt thereof, and optionally an acceptable carrier, excipient, or buffer for oral administration.

2. A kit comprising the corn position of claim 1.

3. The kit of claim 2, wherein the pilocarpine is a pilocarpine product extracted from *Pilocarpus microphyllus*.

4. The kit of claim 2, wherein the pilocarpine is substantially pure.

5. The kit of claim 2, wherein the pilocarpine is pilocarpine hydrochloride.

6. The kit of claim 2, wherein the total pilocarpine concentration in the composition is between 0.01% and 4%.

7. The kit of claim 2, wherein the composition is a gum.

8. The kit of claim 7, wherein the amount of nicotine or a slat thereof is between 1 mg and 4 mg.

9. The kit of claim 2, wherein the composition is formulated for oral delivery.

10. The composition of claim 1, wherein the pilocarpine is a pilocarpine product extracted from *Pilocarpus microphyllus*.

11. The composition of claim 1, wherein the pilocarpine is substantially pure.

12. The composition of claim 1, wherein the pilocarpine is pilocarpine hydrochloride.

13. The composition of claim 1, wherein the total pilocarpine concentration in the composition is between 0.01% and 4%.

14. The composition of claim 1, wherein the composition is a gum.

15. The composition of claim 1, wherein the composition is formulated as a chewing gum.

* * * * *

UNITED STATES PATENT AND TRADEMARK OFFICE
CERTIFICATE OF CORRECTION

| | |
|---|---|
| PATENT NO. | : 11,890,278 B2 |
| APPLICATION NO. | : 16/962827 |
| DATED | : February 6, 2024 |
| INVENTOR(S) | : Roger L. Papke et al. |

It is certified that error appears in the above-identified patent and that said Letters Patent is hereby corrected as shown below:

In the Claims

In Claim 2, at Column 42, Line 1:
"A kit comprising the corn position of claim 1."

Should be replaced with:
--A kit comprising the composition of claim 1.--

In Claim 8, at Column 42, Line 13:
"a slat thereof is between 1 mg and 4 mg."

Should be replaced with:
--a salt thereof is between 1 mg and 4 mg.--

Signed and Sealed this
Ninth Day of April, 2024

*Katherine Kelly Vidal*

Katherine Kelly Vidal
*Director of the United States Patent and Trademark Office*